(12) United States Patent
Couderc et al.

(10) Patent No.: US 7,623,910 B2
(45) Date of Patent: Nov. 24, 2009

(54) ECG-BASED DIFFERENTIATION OF LQT1 AND LQT2 MUTATION

(75) Inventors: Jean-Philippe Couderc, Rochester, NY (US); Martino Vaglio, Biella (IT)

(73) Assignee: University of Rochester, Rochester, NY (US)

( * ) Notice: Subject to any disclaimer, the term of this patent is extended or adjusted under 35 U.S.C. 154(b) by 304 days.

(21) Appl. No.: 11/685,016

(22) Filed: Mar. 12, 2007

(65) Prior Publication Data

US 2008/0033313 A1 Feb. 7, 2008

Related U.S. Application Data

(60) Provisional application No. 60/780,854, filed on Mar. 10, 2006.

(51) Int. Cl.
*A61B 5/04* (2006.01)
(52) U.S. Cl. .................. 600/509; 600/513; 600/516
(58) Field of Classification Search .............. None
See application file for complete search history.

(56) References Cited

OTHER PUBLICATIONS

Matti Viitasalo, MD et al. "Ratio of Late to Early T-Wave Peak Amplitude in 24-h Electrocardiographic Recordings as Indicator of Symptom History in Patients With Long-QT Syndrome Types 1 and 2." Journal of the American College of Cardiology, 47:112-120, doi:10.1016/j.jacc.2005.07.068 (Published online Dec. 13, 2005). Jul. 13, 2009.*

J. K. Kanters, et al, T wave morphology analysis distinguishes between KvLQT1 and HERG mutations in long QT syndrome, Heart Rhythm (2004) 3, 285-292.

Yan, G.X., et al, "Cellular basis for the normal T wave and the electrocardiographic manifestations of the long-QT syndrome," Circulation, vol. 98, No. 18, pp. 1928-1936, Nov. 1998.

Zareba, W., et al,"Influence of genotype on the clinical course of the long-QT syndrome. International Long-QT Syndrome Registry Research Group,"N.Engl.J.Med., vol. 339, No. 14.

Zareba, W., et al, "Location of mutation in the KCNQ1 and phenotypic presentation of long QT syndrome," J.Cardiovasc. Electrophysiol., vol. 14, No. 11, pp. 1149-1153, Nov. 2003.

(Continued)

*Primary Examiner*—Mark W Bockelman
*Assistant Examiner*—Elizabeth K So
(74) *Attorney, Agent, or Firm*—Heslin Rothenberg Farley & Mesiti P.C.; Christopher B. Miller

(57) ABSTRACT

A method differentiating LQT1 mutation from LQT2 mutation is disclosed. An ECG signal is obtained for a patient. At least a first ECG parameter and a second ECG parameter are determined from the ECG signal. A probability that the patient is an LQT1 carrier or an LQT2 carrier is determined based on a regression model which takes into account the first ECG parameter and the second ECG parameter. A system for assessing repolarization abnormalities is also disclosed. The system has a processor configured to differentiate between LQT1 and LQT2 based on at least two ECG parameters from ECG data. The system also has a data input coupled to the processor and configured to provide the processor with the ECG data. The system further has a user interface coupled to either the processor or the data input.

28 Claims, 9 Drawing Sheets

OTHER PUBLICATIONS

Couderc, J.P.,et al,"Identification of sotalol-induced changes in repolarization with T wave area-based repolarization duration parameters,"J.Electrocardiol., vol. 36, Suppl.

Vaglio,M., et al,"Fractionated repolarization velocity induced by sotalol in healthy subjects," Computers in Cardiology 2005 32, 523-526 2005.

Priori, S.G., et al, "Evaluation of the spatial aspects of T-wave complexity in the long-QT syndrome," Circulation, vol. 96,No. 9,pp. 3006-3012,Nov. 1997.

Zabel,M.,et al,"Analysis of 12-lead T-wave morphology for risk stratification after myocardial infarction," Circulation,vo.12,No. 11,pp. 1252-1257,Sep. 2000.

Zabel,M.,et al,"Analysis of T-wave morphology from the 12-lead electrocardiogram for prediction of long-term prognosis in male US veterans,"Circulation,vol. 105,No. 9,pp. 1066-1070.

Press,W.H.,et al,"Numerical recipes in C: The Art of Scientific Computing," Second ed., Cambridge University Press, 1992.

Kanters;J.K.,et al,"T wave morphology analysis distinguishes between KvLQT1 and HERG mutations in long QT syndrome,"Heart Rhythm,vol. 1,No. 3, pp. 285-292,Sep. 2004.

Struijk,J.J.,et al,"Classification of the long QT syndrome based on discriminant analysis of T-wave morphology,"Computers in Cardiology 2005 32, 511-514, 2005.

Kutner, M.H., et al, "Applied Linear Regression Models," 4th ed. New York: McGraw-Hill/Irwin, 2004, pp. 582-585.

Badilini,F.,et al,"QT interval analysis on ambulatory electrocardiogram recordings: a selective beat averaging approach,"Med.Biol.Eng Comput., vol. 37, No. 1, pp. 71-79, Jan. 1999.

Lehmann,M.H.,et al,"Sexual dimorphism in the electrocardiographic dynamics of human ventricular repolarization: characterization in true time domain,"Circulation,vol. 104,No. 1.

Lehmann,M.H., et al,"T wave 'humps' as a potential electrocardiographic marker of the long QT syndrome,"J Am Coll Cardiol,vol. 24,No. 3,pp. 746-754,Sep. 1994.

Malfatto,G.,et al,"Quantitative analysis of T wave abnormalities and their prognostic implications in the idiopathic long QT syndrome,"J Am Coll Cardiol,vol. 23,No. 2,pp. 296-301.

Moss,A.J.,et al,"ECG T-wave patterns in genetically distinct forms of the hereditary long QT syndrome,"Circulation,vol. 92,No. 10,pp. 2929-2934,Nov. 1995.

Schwartz,P.J., et al, "Diagnostic criteria for the long QT syndrome. An update," Circulation, vol. 88, No. 2, pp. 782-784, Aug. 1993.

Couderc,J.P.,et al,"Drug-induced changes of ventricular repolarization: New incentives for quantifying T wave morphology,"Malmivuo,J. and Kauppinen,p. 5[1],167-70.2003.

Couderc,J.P.,et al,"T-wave morphology and arrhythmic events in patients with dilated cardiomyopathy,"Computers in Cardiology 2003 30, 149-152. 2003.

Priori,S.G.,et al,"Risk stratification in the long-QT syndrome," N. Engl J Med May 8, 2003; 348(19): 1866-1874.

Zhang,L,et al,"Spectrum of ST-T-wave patterns and repolarization parameters in congenital long-QT syndrome:ECG findings identify genotypes,"Circulation Dec. 5, 2000;102(23):2849.

Priori, S.G., et al, "Low Penetrance in the Long-QT Syndrome: Clinical Impact, "Circulation Feb. 2, 1999;99(4):529-533.

Moss, A.J., et al,"Effectiveness and limitations of beta-blocker therapy in congenital long-QT syndrome," Circulation Feb. 15, 2000;101(6):616-623.

Schwartz, P.J., et al,"Left cardiac sympathetic denervation in the management of high-risk patients affected by the long-QT syndrome ,"Circulation Apr. 20, 2004;109(15):1826-1833.

Viskin,S.,"Cardiac pacing in the long QT syndrome: review of available data and practical recommendations," J Cardiovasc Electrophysiol May 2000;11(5): 593-600.

Zareba, W., et al,"Implantable cardioverter defibrillator in high-risk long QT syndrome patients,"J Cardiovasc Electrophysiol Apr. 2003;14(4):337-341.

Napolitano, C.,et al,"Genetic testing in the long QT syndrome: development and validation of an efficient approach to genotyping in clinical practice,"JAMA Dec. 21, 2005;294(23).

Priori, S.G., et al, "Association of long QT syndrome loci and cardiac events among patients treated with beta-blockers," JAMA Sep. 15, 2004;292(11):1341-1344.

Couderc, J.P., et al,"Repolarization morphology in adult LQT2 carriers with borderline prolonged QTc interval," Heart Rhythm 2006.

Merri, M., et al, "Electrocardiographic quantitation of ventricular repolarization," Circulation Nov. 1989; 80(5):1301-1308.

Padrini, R., et al, "Morphological algebraic models of the TU-wave patterns/in idiopathic long QT syndrome," Int J Cardiol Feb. 2001;77(2-3):151-162.

Merri,M.,et al,"Relation between ventricular repolarization duration and cardiac cycle length during 24-hour Holter recordings. Findings in normal patients and patients . . . ".

Benhorin, J., et al, "Long QT syndrome. New electrocardiographic characteristics," Circulation Aug. 1990;82(2):521-527.

Benhorin, J., et al,"Evidence of genetic heterogeneity in the long QT syndrome," Science Jun. 25, 1993;260(5116):1960-1962.

Zareba, W., et al, "TU wave area-derived measures of repolarization dispersion in the long QT syndrome," J Electrocardiol 1998;30 Suppl:191-195.

Couderc, J.P., et al,"Electrocardiographic method for identifying drug-induced repolarization abnormalities associated with a reduction of the rapidly activating delayed . . . ".

Badilini, F., et al, "Quantitative aspects of ventricular repolarization: relationship between three-dimensional T wave loop morphology and scalar QT dispersion," Ann Noninvas.

Extramiana, F., et al,"Clinical assessment of drug-induced QT prolongation in association with heart rate changes," Clin Pharmacol Ther Apr. 2005;77(4) 247-258.

* cited by examiner

Population characteristics and classical ECG parameters

|  | LQT1 | LQT2 |
| --- | --- | --- |
| N (females) | 49 (69%) | 25 (76%) |
| Betablockers (%) | 63 | 44 |
| RR (ms) | 849 ± 110 | 837 ± 134 |
| QT (ms) | 450 ± 38 | 466 ± 70 |
| QTcF (ms) | 478 ± 29 | 494 ± 49 |
| QTc B (ms) | 493 ± 29 | 510 ± 41 |
| TpTe (ms) | 87 ± 8.0 | 112 ± 24 * |
| $QT_{apex}$ (ms) | 363 ± 35 | 354 ± 65 |
| Tmag (mV) | 0.34 ± 0.15 | 0.12 ± 0.14 * |

Measurements are from lead V5. QTc B: heart corrected QT using Bazet's formula, QTc F: QTc corrected using Fridericia formula. * Kruskal-Wallis nonparametric test; statistical significance ($p \leq 0.02$).

|  | LQT1 | LQT2 |
|---|---|---|
| N | 49 | 25 |
| RR (ms) | 849 ± 110 | 837 ± 134 |
| Loop QT (ms) | 452 ± 37 | 465 ± 62 |
| $\lambda_2/\lambda_1$ | 0.233 ± 0.097 | 0.368 ± 0.147 * |
| $\lambda_3$ | 0.045 ± 0.020 | 0.081 ± 0.031 * |
| MV (mV) | 0.98 ± 0.39 | 0.44 ± 0.18 * |
| αL on $ev_1$ (μV/ms) | 8.2 ± 2.9 | 3.6 ± 1.5 * |
| αR on $ev_1$ (μV/ms) | -12.2 ± 4.5 | -4.1 ± 2.1 * |
| Hill $V_{max}$ (mV·s) | 0.168 ± 0.077 | 0.098 ± 0.054 * |
| Hill n | 5.1 ± 2.1 | 4.7 ± 2.7 * |
| Hill $K_m$ (s) | 0.25 ± 0.04 | 0.26 ± 0.07 |

*Kruskal-Wallis nonparametric test; statistical significance ($p \leq 0.02$).

FIG. 3A

PCA and T-wave modeling parameters, HR 75-77.5 bpm

|  | LQT1 | LQT2 |
|---|---|---|
| N | 48 | 23 |
| RR (ms) | 788 ± 3 | 788 ± 3 |
| QT (ms) | 441 ± 28 | 451 ± 43 |
| TpTe (ms) | 84 ± 11 | 109 ± 32 * |
| Tmag (mV) | 0.33 ± 0.14 | 0.11 ± 0.16 * |
| Loop QT (ms) | 442 ± 26 | 456 ± 45 |
| Loop QTa (ms) | 353 ± 26 | 330 ± 42 |
| $\lambda_2/\lambda_1$ | 0.22 ± 0.09 | 0.36 ± 0.17 * |
| $\lambda_3$ (mV) | 0.046 ± 0.020 | 0.082 ± 0.036 * |
| $\alpha L$ on $ev_1$ (µV/ms) | 8.0 ± 3.0 | 3.6 ± 1.7 * |
| $\alpha R$ on $ev_1$ (µV/ms) | -12.7 ± 5.1 | -4.3 ± 2.6 * |
| MV (mV) | 0.95 ± 0.38 | 0.45 ± 0.19 * |
| Hill Vmax (mV·s) | 0.16 ± 0.07 | 0.10 ± 0.05 * |
| Hill n | 5.28 ± 2.86 | 4.55 ± 3.79 * |
| Hill Km (s) | 0.24 ± 0.03 | 0.24 ± 0.06 |

Kruskal-Wallis nonparametric test; statistical significance ($p \leq 0.01$).

FIG. 3B

Gender characteristics of the two mutations, HR 75 – 77.5 bpm

|  | LQT1 (N=48) |  | LQT2 (N=23) |  |
| --- | --- | --- | --- | --- |
| Gender | F (N=34) | M (N=14) | F (N=17) | M (N=6) |
| RR (ms) | 787 ± 2 | 789 ± 3 | 787 ± 2 | 789 ± 2 |
| QT (ms) | 443 ± 29 | 437 ± 28 | 456 ± 44 | 434 ± 41 |
| Qtapex (ms) | 361 ± 28 | 349 ± 20 † | 349 ± 35 | 322 ± 52 |
| TpTe (ms) | 82 ± 8 | 89 ± 15 † | 108 ± 26 | 113 ± 28 |
| T mag (mV) | 0.31 ± 0.12 | 0.38 ± 0.18 | 0.12 ± 0.16 | 0.07 ± 0.13 |
| $\alpha L$ on $ev_1$ ($\mu V/ms$) | 7.5 ± 2.4 | 9.3 ± 3.9 † | 3.8 ± 1.8 | 3.1 ± 1.4 |
| $\alpha R$ on $ev_1$ ($\mu V/ms$) | -11.7 ± 4.2 | -15.3 ± 6.2 † | -4.8 ± 2.8 | -2.8 ± 1.3 |
| MV (mV) | 0.84 ± 0.27 | 1.22 ± 0.49 * | 0.46 ± 0.20 | 0.40 ± 0.18 |

*Kruskal-Wallis nonparametric test; * $p<0.05$, † $p<0.09$.

Description of the logistic models for the discrimination of LQT1 and LQT2 patients

|  | Cst. | 1st parameters | 2nd parameter | 3rd parameter | Pr(LQT2) threshold |
|---|---|---|---|---|---|
| Clinical model | 81.071 | QT (0.009490) | RR (-0.1092) |  | > 0.36 |
| Scalar model | -7.187 | T magnitude (-15.70) | TpTe (0.1023) |  | > 0.4 |
| Vectorial model | 11.73 | αR on $ev_1$ (-1352) | Loop QT offset (0.2480) | $QT_{peak}$ LII (-0.3163) | > 0.32 |

Cst: constant of the binary logistic model. Each cell of the table contains the name of the parameter and the associated coefficient for this specific parameter.

FIG. 5

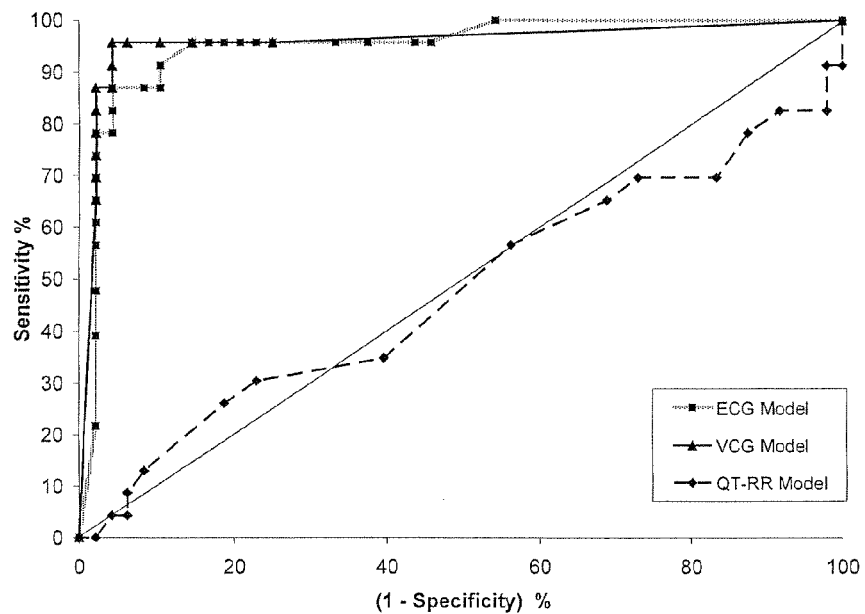

FIG. 6

ECG-BASED DIFFERENTIATION OF LQT1 AND LQT2 MUTATION

RELATED APPLICATIONS

This application claims priority to U.S. provisional patent application 60/780,854, entitled "Quantitative Repolarization Patterns Identifying KvLQT1 and HERG Mutation in Patients with Long QT Syndrome", and filed Mar. 10, 2006. The entire 60/780,854 patent application is hereby officially incorporated by reference.

This invention was made with government support under grant HL068226 and HL033843 awarded by NIH. The government has certain rights in the invention.

FIELD

The claimed invention relates to Electrocardiogram-based analysis systems and methods. More particularly, the claimed invention relates to ECG-based differentiation of LQT1 and LQT2 mutation in patients.

BACKGROUND

The electrocardiogram (ECG) is based on the electrical activity of the heart muscle cells. In the resting stage, the inside of the cardiac cells has a negative charge compared to the outside of the cells. The resulting voltage difference between the internal and the external spaces of the cell membrane is called transmembrane potential. The discharging of this voltage is known as depolarization and is associated with the start of the contraction of the heart muscle cell fibers. After contraction of the ventricles, the heart muscle cells redevelop substantially the same voltage over the cell membrane. This recovery phase is called the repolarization process of the heart ventricles. An ECG measured from the skin surface measures a total electrical component created by the depolarization and repolarization of the heart's muscular cells.

The repolarization of the heart is made possible in part by ion channels within the myocardial cells of the heart which allow an ion current to redistribute charge. It is highly important that the regulation of the ion currents during the ventricular repolarization process occurs without interference, since a delay in this process or any other abnormalities can lead to a substantially increased risk for sudden cardiac death.

Medical professionals have used electrocardiograms (ECG's) to examine the ventricular repolarization period, also known as the QT interval, to check for elongation of the QT interval. In general, an elongated QT interval may be considered to be indicative of a delay in the ventricular repolarization process. While medications in some cases may be the cause of an elongated QT interval, for many people are predisposed to have an elongated QT interval due to one or more congenital mutations. Those patients having a congenital predisposition for an elongated QT interval are referred-to as having Long QT Syndrome, or LQTS. The clinical course and the precipitating risk factors in the congenital Long QT Syndrome (LQTS) are genotype specific. Among LQTS mutations, KvLQT1 (LQT1) and HERG (LQT2) mutations have the higher likelihood of recurrent cardiac events and their diagnosis is crucial to reduce lethal outcome.

The Long QT Syndrome (LQTS) is an inherited disease caused by genetically determined defects in trans-membrane ion channel subunit. LQTS patients are at high risk of sudden cardiac death due to the development of ventricular tachycardia degenerating in ventricular fibrillation and cardiac arrest. The prevalence of the syndrome may be expected to occur in 1 in 3000-5000 individuals per year in the United States. The number of cases of sudden cardiac death associated with the LQTS is unknown but among the 300,000 sudden cardiac deaths documented each year, one may expect around 2-5% having LQTS-related arrhythmic death. In the US, the syndrome remains an under diagnosed disorder because an estimated 10 to 15% of the LQTS gene carrier patients have a QT interval duration near normal values.

Seven mutant genes have been associated with LQTS: KvLQT1/minK, HERG, SCN5A, Ankyrin B, KCNE1, KCNE2 and KCNJ2. Most of these genes encode cardiac ion channels and their mutation leads to dysfunction of the ion current kinetics. Among the current 150 mutations identified in the seven LQTS genes, LQT1 and LQT2 represent the majority of cases (88%) whereas LQT3 account for (7%) and the others are very rare. Typically in these types of LQTS, the arrhythmias occur in conjunction with vigorous physical exercise and emotional stress. The mutation of the HERG (LQT2) gene decreases the rapidly activating delayed rectifier potassium (K+) current (IKr). KvLQT1 mutation (LQT1) is associated with blockade of the slowly activating delayed rectifier K+ currents (IKs). The inhibition of IKr/IKs ion currents is associated with a prolongation of the action potentials within the heart leading in general to a prolonged QT interval on the surface ECGs.

Once a patient is identified as having an elongated QT interval, there is still a clinical need for discriminating mutation-specific syndrome (LQT1 vs. LQT2 patients) because of the mutation-specific therapeutic strategies one may consider. In this case, the QT/QTc prolongation is not a useful marker, the QT interval is, in average, prolonged similarly within the two groups. Traditionally, genetic testing has been prescribed to determine which form of Long QT Syndrome is the cause. Unfortunately, genetic testing can cost thousands of dollars and is time consuming. The expense of the testing alone prevents many patients from receiving important information about the root cause of their elongated repolarization interval. Therefore, there exists a need for an economical, reliable, and quicker way to differentiate between patients with the LQT1 and LQT2 mutation.

SUMMARY

A method differentiating LQT1 mutation from LQT2 mutation is disclosed. An ECG signal is obtained for a patient. At least a first ECG parameter and a second ECG parameter are determined from the ECG signal. A probability that the patient is an LQT1 carrier or an LQT2 carrier is determined based on a regression model which takes into account the first ECG parameter and the second ECG parameter.

A system for assessing repolarization abnormalities is also disclosed. The system has a processor configured to differentiate between LQT1 and LQT2 based on at least two ECG parameters from ECG data. The system also has a data input coupled to the processor and configured to provide the processor with the ECG data. The system further has a user interface coupled to either the processor or the data input. It is at least one goal of the claimed invention to provide an improved method and system for the identification and differentiation of LQT1 and LQT2 mutations in patients.

BRIEF DESCRIPTION OF THE DRAWINGS

FIGS. 2A-4 illustrate experimental results related to ECG parameters and LQT1 vs LQT2 mutation.

FIG. 5 illustrates one embodiment of a logistic model for the discrimination of LQT1 and LQT2 patients.

FIGS. 6-7 schematically illustrate the effectiveness of certain embodiments of predictive models.

Figure 1A:
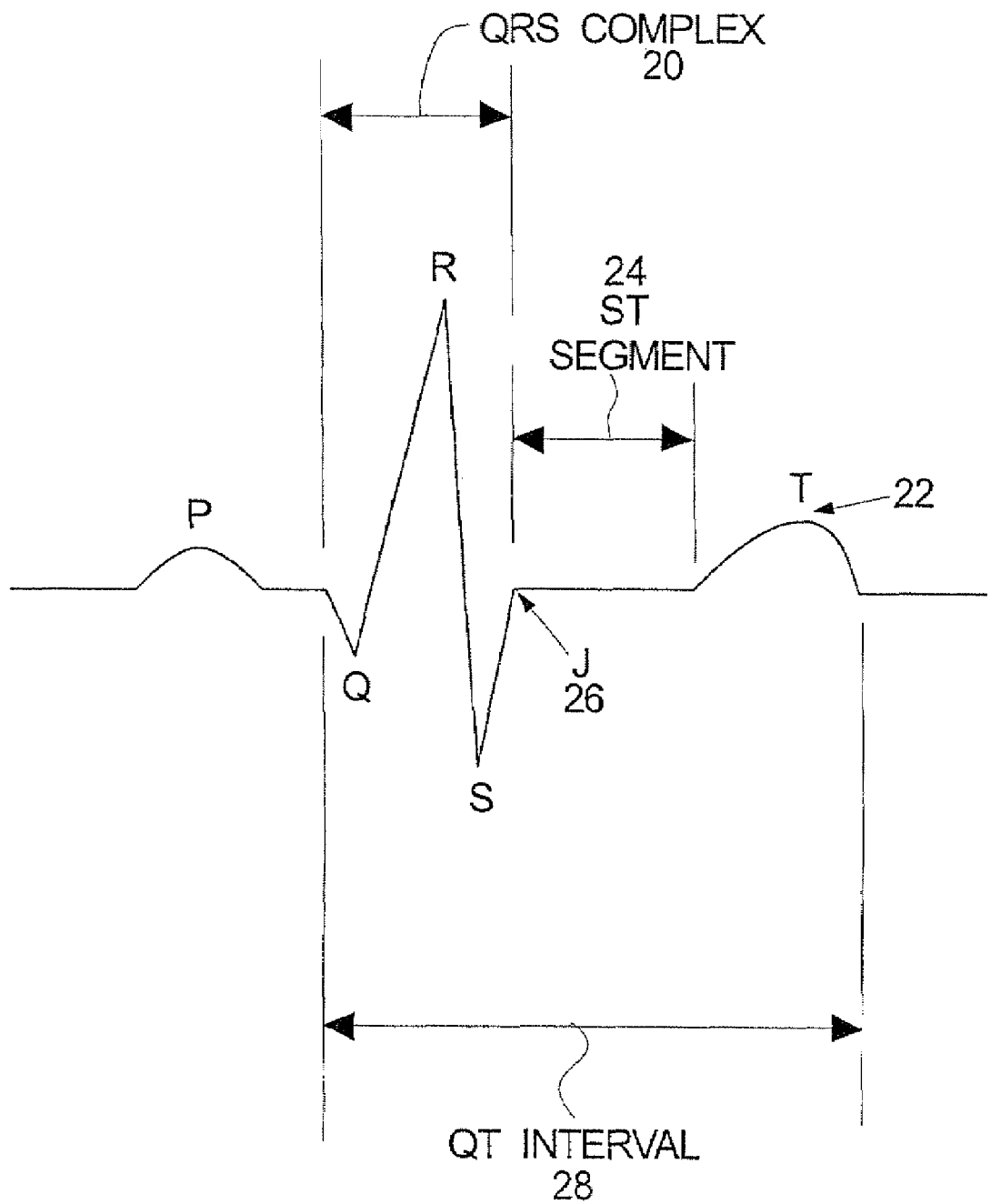
FIGS. 1A-1C schematically illustrate embodiments of a heartbeat and some scalar and vector-based parameters which can be determined from ECG signals.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

A surface electrocardiogram (ECG) may be measured by an ECG capture device which can have one or more leads which are coupled to a person's body in various locations. The electrical activity occurring within individual cells throughout the heart produces a cardiac electrical vector which can be measured at the skin's surface by the ECG capture device leads. The signal registered at the skin's surface originates from many simultaneously propagating activation fronts at different locations, each of which affects the size of the total component. One type of ECG capture device is a twelve-lead signal device, although ECG capture devices of any number of leads may be used to gather a set of ECG signals for use in assessing repolarization abnormality.

FIG. 1A schematically illustrates an embodiment of an ECG showing one heart beat and some of the labels which are commonly assigned to various portions of the ECG signal. The QRS complex 20 is associated with the depolarization of the heart ventricles. The QT interval 28 and the T-wave 22 are associated with repolarization of the heart ventricles. The ST segment 24 falls between the QRS complex 20 and the T-wave 22. The J point 26 is located where the QRS complex 20 joins the ST segment 24. For reference, the QT interval 28 discussed above, and which may be an indicator of Long QT Syndrome, is illustrated.

Figure 1B:
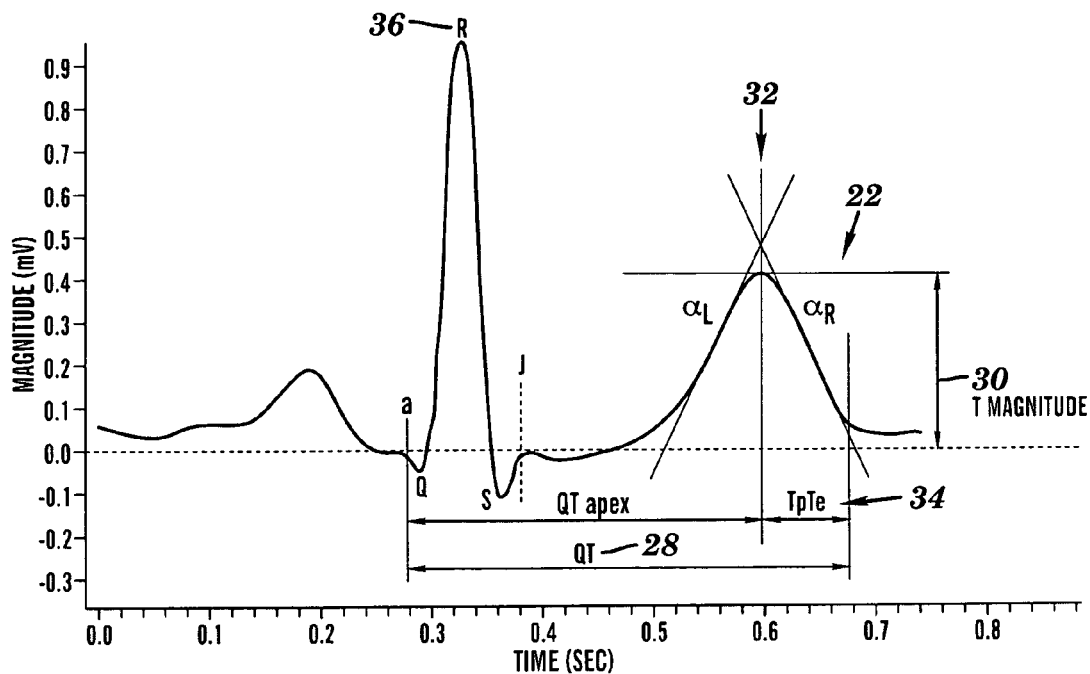

FIG. 1B schematically illustrates another embodiment of an ECG showing one heart beat and some scalar metrics which may be determined for various portions of the ECG signal. For reference, the QT interval 28 is illustrated again, as occurring from the start of the QRS complex and going until the end of the T wave 22. There are various ways of determining the end of the T-wave 22. Here, a right slope αR of the T-wave 22 is projected down to the baseline voltage, and where the right slope αR of the T-wave intersects the baseline voltage (in this case where the right slope αR of the T-wave intersects zero volts) determines the end of the T-wave 22. The T-wave 22 has a Tmagnitude 30 corresponding to the peak of the T-wave 22. The peak of the T-wave 22 occurs at a T-wave peak time 32. The time from the T-wave peak time 32 until the end of the T-wave is defined as the TpTe interval 34. The heartbeat duration RR is measured from one R peak 36 to a next R peak. A peak voltage during the QT interval (QTpeak) may be determined.

Figure 1C:
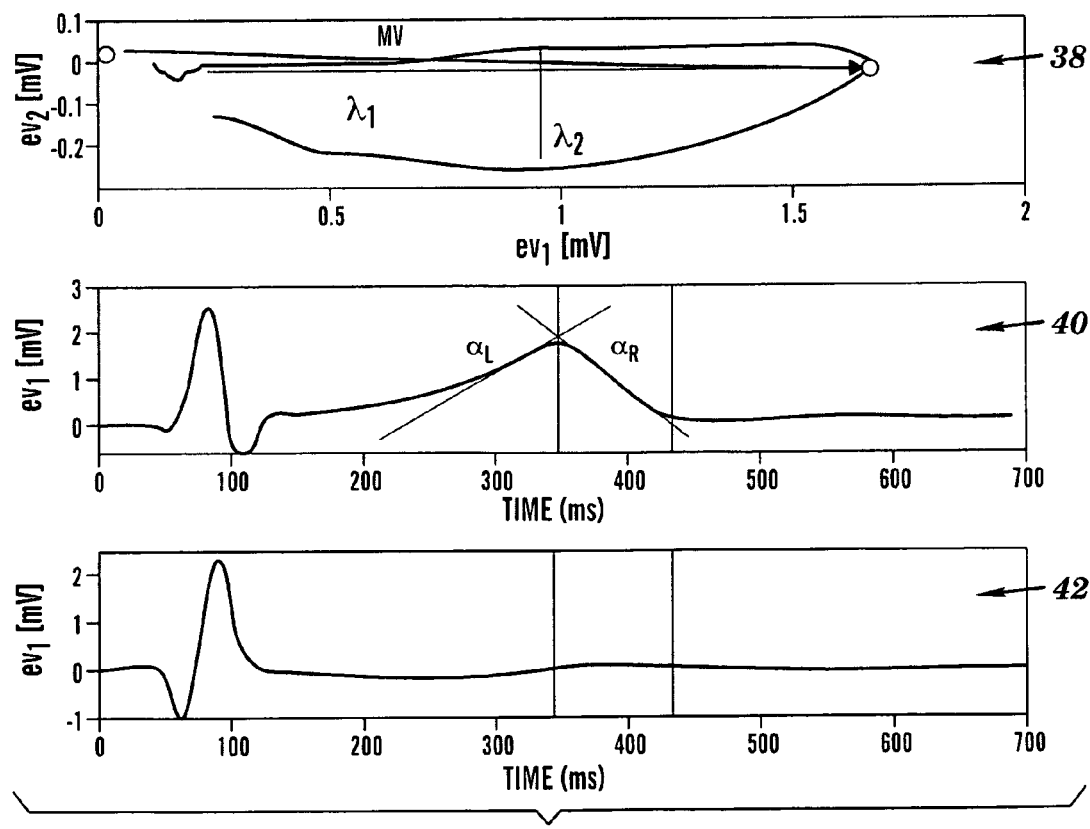

FIG. 1C schematically illustrates an embodiment of data plots based on multiple ECG signals from different ECG capture device leads. Here, primary components analysis is performed on the ECG data to produce a plot of the repolarization interval data in a preferential plane 38 defined by first and second eigenvectors ev1 and ev2. A maximum vector MV can be found for the plotted T-loop. The complexity of repolarization λ2/λ1 may be defined for the T-loop, as well as a Loop QT offset. Such parameters are well known to those skilled in the art and are described here for reference. Additionally, the eigenvector leads ev1 40 and ev2 42 may be computed and plotted versus time. The left slope αL on the T-wave of ev1 40 and the right slope αR on the T-wave of ev1 40 may also be determined.

Using various scalar and vector-based parameters determined from one or more ECG signals, it may be determined whether or not a patient with Long QT Syndrome has the LQT1 genetic mutation or the LQT2 genetic mutation as the cause of the Long QT Syndrome by using a regression model which takes into account at least two of the scalar or vector based ECG parameters.

A study has been done to show the viability of this approach as follows:

Experimental Results:

Population

The study population consists of 49 LQT1 and 25 LQT2 carrier genotyped patients from 26 LQT1 families and 19 LQT2 families. These patients are all enrolled in the International Registry for the LQTS in whom 12-lead Holter ECGs were recorded. The HERG and KvLQT1 mutations were identified in each subject using standard genetic tests.

ECG Recordings

Twenty-four hours 12-lead Holter ECGs were acquired using the H12 recorders from Mortara Instrument (Mortara Instrument, Milwaukee, Wis.). This equipment provides 24-hour Holter digital ECG signal at a sampling frequency of 180 Hz and with 16 bit amplitude resolution (2.5 μV).

Eight true leads are recorded and the remaining four leads (augmented limb leads aVR, aVL, aVF and lead III) were computed.

Measurement Technique

All measurements are based on median beats from 10 consecutive cardiac cycles throughout entire 24-hour Holter recording. Only beats with stable heart rate (HR) are taken into account. The HR-stability assessment was based on the computation of the average HR within the 10 beats. This set of beats was accepted if all beats met the following criterion:

We investigated electrocardiographic and vectorcardiographic parameters in order to better characterize and understand the abnormalities differentiating LQT1 from LQT2 patients. To exclude circadian rhythms influence, we focused our work on the diurnal period.

We measured classical repolarization ECG measurements as the QT interval, Q to Tpeak interval (QTpeak), Tpeak to Tend interval (TpTe) and the magnitude of the T-wave (Tmag) from lead II and lead V5, using our own developed software for Comprehensive Analysis of the repolarization Signal (COMPAS). The vectorcardiographic measurements were based on the Principal Components Analysis (PCA) of the repolarization segment defined between the J point and the point located 220 ms before the next R peak (the shorter one in the set of 10 continuous beats) in order to ensure that the analysis encompasses all components of the ventricular repolarization. Those skilled in the art are familiar with this type of PCA analysis. The PCA analysis was applied to the eight original leads.

Briefly, the method relies on the computation of the singular value decomposition (SVD) [B9], in which any matrix A (M×N) can be written as:

$$A = USV^T$$

where U is a (M×N) column-orthogonal matrix, S is a diagonal matrix with positive or zero elements (the singular values), and V an (N×N) orthogonal matrix containing the right singular vectors.

Being A a matrix (M×8), having in columns the 8 leads and in row the M samples of the repolarization signal of one median cardiac beat, applying SVD, we get U, S and VT matrices; S will contain the 8 eigenvalues in descending order. Multiplying AV, provides the projection of our original data on the principal components.

The repolarization signal within the space defined by the three first components (ev1, ev2, ev3) will be called the T-loop signal, note that it was not constructed from the original orthogonal Frank leads. The evn signals are the eigen-leads. The plane (ev1⊥ev2) defines the preferential plane of the T-loop. Following the dipolar theory of electrocardiography, the T-loop represents the path followed by the cardiac vector (VECG) during the repolarization process of the heart ventricles.

PCA measurements were obtained from the COMPAS PCA analysis package, which offers standard PCA parameters: complexity of repolarization ($\lambda 2/\lambda 1$), T-loop planarity ($\lambda 3$) and other T-wave and T-loop morphology parameters such as the right ($\alpha R$) and left ($\alpha L$) slopes of the T-wave, computed on ev1. It also includes more complex repolarization parameters, based on the morphology of the T-loop in the principal components, such as maximum vector (MV), the interval from beginning on QRS to the instant at MV (LQTa) and QT interval calculated on T-Loop (LQTe), where the end of the T-wave is identified as the point Te:

The end of the T-wave is identified from the T-loop in its preferential plane. The detection of the end of the T-loop is defined as the earliest point of the current beat to meet the two criteria: 1) to be inside the circle of radius equals 25% of MV and centre in the point identified as the projection of the beginning of QRS on the preferential plane and 2) to have a repolarization velocity inferior of 3 mV/s.

Statistical Analysis

The ECG and VCG parameters were analyzed using multivariate analysis involving binary logistic regression to design models selecting the most discriminating parameters in the subset of factors we have investigated. A best subset regression model was selected based on the Akaike Information Criterion. Averaged values of parameters were compared using non-parametric test (Kruskal-Wallis). A p-value<0.05 was considered statistically significant.

We use an analytical strategy in which a referential model based on classical ECG parameters is first implemented then, a second model including both classical and vectocardiographic parameters quantifying T-wave and T-loop morphology is investigated.

The comparison between models is based on the area under the curve (AUC) of the receiver operating characteristics (ROC). The ROC curves are obtained by varying the threshold on the probability of being LQT2 patient from 0 to 1, this probability for each patient is provided by the binary logistic model.

Results

The clinical characteristics of the study population and the values from the 12-lead ECG parameters for the two populations are summarized in FIG. 2. There were 35 females in LQT1 (71%) and 19 females in LQT2 (76%). The average ages were 34.3±10.2 yrs for LQT1 and 35.5±9.4 yrs for LQT2. Average RR intervals (from standard 12-lead 24 h Holter) were similar between LQT1 (906±193 ms) and LQT2 (904±211 ms) patients. 31 LQT1 and 11 LQT2 were on beta blockers the day their Holter ECG was recorded. The distribution of gender and the percentage of patients on beta-blocking therapy were not statistically different between both groups.

Figures 2A, 2B:
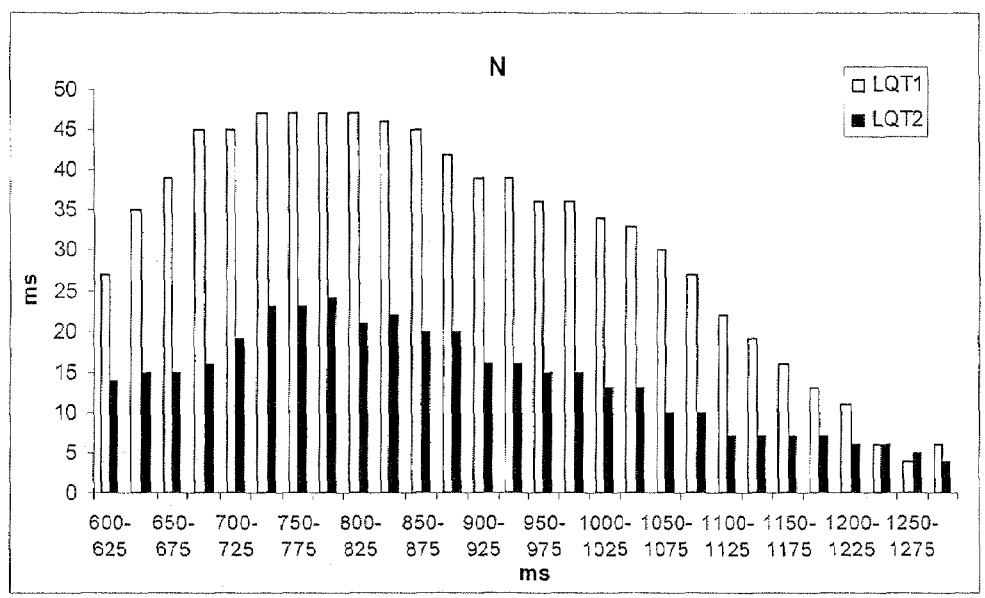

The role of heart rate (HR) on the repolarization measurements is fundamental regardless of the type of measurements one can consider. In the discrimination between LQT1 and LQT2 patients, the effect of HR cannot be neglected even if in average the HR is not significantly different between the two types of mutations (FIG. 2A). Because we have access to 24-hour Holter ECGs, we can compare QT interval values between the two populations at similar heart rate. The technique called "Bin Analysis" allows for controlling the effect of HR on repolarization measurements. It resides in selective technique in which median cardiac beats are gathered when they are in a specified limited HR range. Repolarization measurements are computed on these beats and the results are averaged. Averages are reported for all limited HR ranges available within the recordings. FIG. 2B describes the HR ranges. We considered in this study intervals ranging from RR=600 ms to 1300 ms by steps of 25 ms. As shown in FIG. 2B the distribution of individuals presenting cardiac beats in the studied range of HR is similarly distributed between the two groups. Only HR ranges centered on very low heart rate had a number of individual not large enough to ensure statistical power.

Initially, we focused our investigation on the limited HR range in which the number of subjects was maximal for the two groups. We chose the range in which RR interval varies from 775 ms to 800 ms corresponding to an HR between 75 and 77.5 bpm. One LQT1 and two LQT2 subjects were excluded from the analysis because they did not have any cardiac beat in this HR range.

FIG. 3A provides the values of the investigated repolarization parameters in the LQT1 and LQT2 populations when considering uncorrected average values from the overall diurnal period of the recordings.

FIG. 3B provides the results from all repolarization measurements realized in LQT1 and LQT2 populations for the HR range discussed in the previous paragraph. There is no large difference between results when considering overall mean values and values from the HR range we have selected. The QT interval prolongation was similar between the two mutations and all statistically significant differences between the two groups are present.

Figures 3C, 4:
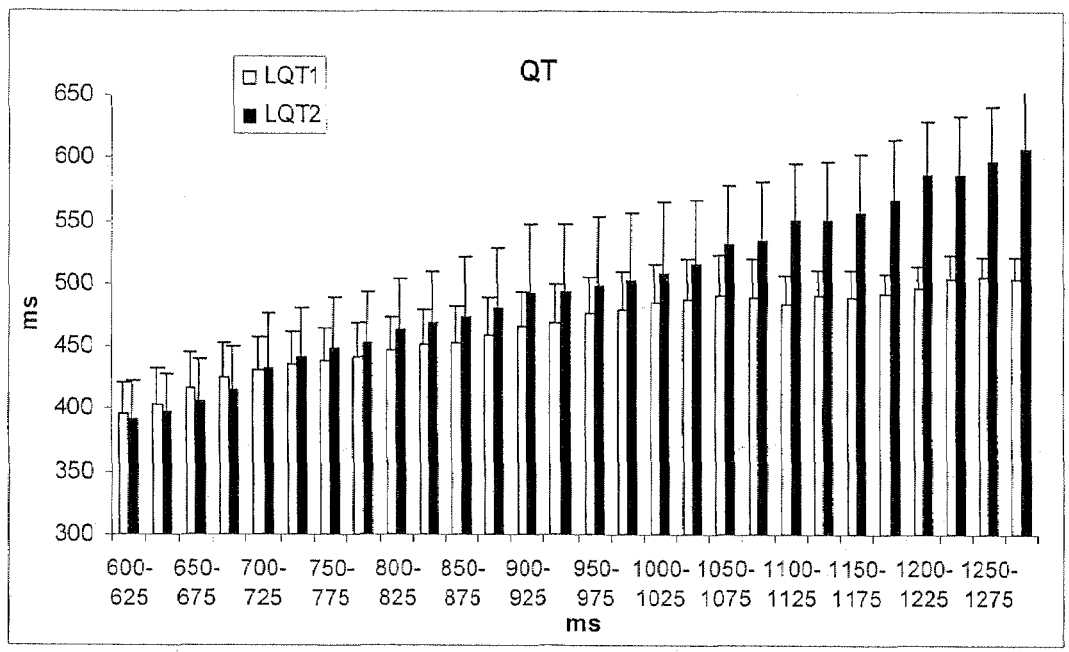

Based on median beat measurements from the Holter ECG recording, FIG. 3C shows QT interval distribution across heart rate for the two populations. For RR<1000 ms, QT (v5) interval duration for the two LQTS population is very similar (443±36 ms for LQT1 and 456±60 ms for LQT2, p=0.4), while for RR>1025 ms, LQT2 have a significantly longer QT interval durations than LQT1 patients (492±30, 529±63 ms, p=0.05), revealing a more pronounced presence of specific repolarization morphologies in Holter ECGs.

As previously described the LQT2 patients present very low and flat T-waves. In our study, these results are confirmed by revealing different values between the two groups in terms of T-wave slopes and MV values. LQT1 have taller T-wave: 0.33±0.14 mV vs. 0.11±0.16 mV for LQT1 and LQT2 patients respectively (p<0.05) and steeper slopes. Right and left slopes of T-wave were almost three fold higher in LQT1 patients: 8.0±3.0 vs. 3.6±1.7 µV/ms in LQT1 and LQT2 for the left slope and 12.7±5.1 vs. 4.3±2.6 µV/ms for the right slope.

The right slope of T-wave is the best parameter for the discrimination between LQT1 and LQT2 patients, with AUC=0.95 and 87.5% specificity and 87% sensitivity.

T-wave magnitude in lead V5 was the best classical ECG parameter, with AUC=0.85 and 73.9% specificity and 78.3% sensitivity.

Other vectorial parameters such as T-loop roundness and T-loop planarity were significantly higher in LQT2 than in LQT1, revealing a profound difference in the repolarization process affecting the overall orientation and electrical activity within the myocardium between the two mutations.

The morphology of the T-wave is different between males and females. We investigated the role of gender in the two LQTS populations. These results are summarized in FIG. 4. Several T-wave morphologic parameters are significantly different in LQT1 between the two genders, especially the slopes of the T-wave and MV, indicating taller and steeper T-wave in males which confirm prior results on sexual dimorphism of the T-wave. Such differences were not found in the ECG signals of LQT2 carriers reinforcing the profound impact of the IKr reduction on the surface ECGs.

Statistical Model for the Discrimination Between LQT1 and LQT2 Patients: Multivariate Analysis First, we designed a model based on clinical parameters (QT, and RR), then added all the scalar ECG parameters and finally introduced the vectorial parameters. FIG. 5 provides the coefficients of the various binary logistic models developed on our study population. The last column describes the thresholds for the probability of being a LQT2 patients leading to the results describe in the following paragraphs. These models were designed based on the repolarization measurement within the heart range: 75 and 77.5 bpm.

Clinical Model

This model has been implemented as a reference. It describes the level of discriminant power obtained when using our statistical strategy and when only QT and RR intervals are used, the currently used clinical electrocardiographic parameters. As expected, this model performed poorly (see. FIG. 6).

Scalar Model

The parameters included in the model were: RR, QTpeak, TpTe, T-wave magnitude and QT from lead II and V5. Using the best subset model based on the AIC criteria, a model using 2 parameters (Tmag and TpTe from lead V5) was selected. The model provided a good discrimination of the two mutations: 95.8% specificity and 87.0% sensitivity.

Vectorial Model

The design of the computerized model was based on the following list of repolarization parameters: parameters from scalar model and $\lambda 2/\lambda 1$, $\lambda 3$, right and left slope of T-wave from lead ev1, MV, Loop QT, Loop QTapex and 3 parameters from T-wave modeling with Hill equation. The best model with three parameters relied on the following ones: $\alpha R$, QTpeak from Lead II and QT interval from the T-loop could discriminate the two groups with 95.8% specificity and 95.7% sensitivity, for LQT2 prediction.

FIG. 6 shows the ROC curves for the three models. As expected, the QT-RR model has a very poor discriminant power (AUC=0.60), a random selection would have AUC equal to 0.5. The vectrocardiographic model presents highest AUC: 0.995, slightly higher than 0.959 for the ECG model. In the following paragraphs the comparison will be computed only between scalar and vectorial models.

Evaluation in a Wider HR Range

We evaluated the stability of our predictive models for larger HR intervals to partially assess the validity of the models. We fitted the current models with data from larger ranges of heart rate. We defined three HR ranges:

HR<60 bpm (RR>1000 ms)
$60 \leq HR < 92$ bpm ($650 < RR \leq 1000$ ms)
$HR \geq 92$ bpm ($RR \leq 650$ ms)

Figure 7:
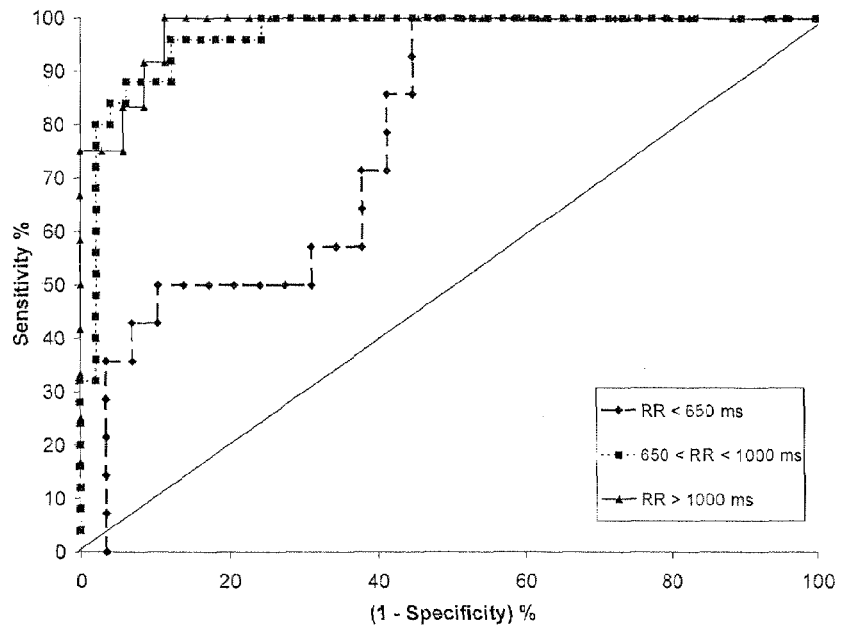

The ROC curves for the scalar model are presented in FIG. 7. For very high HR (HR>92 bpm), both models have low discriminant power. The scalar model had very high discriminate power for HR below 92 bpm, while the vectorial model had even better performances for HR between 60 and 92 bpm.

The information contained in the morphology of the T-wave from both scalar ECG and vectorcardiographic signals are relevant in discriminating the patients according to their type of mutations (HERG vs. KvLQT1). In particular, we observed that HERG patients present lower values of MV (related to T-wave magnitude in all scalar leads), this can also be assessed using the left and right slopes of T-wave (flatter T-wave). T, and the TpTe interval is significantly longer than in LQT1 patients. These results are consistent with previous work.

T-wave magnitude and MV show very different heart rate dependency between mutations. In LQT2, there is almost no HR dependency, while in LQT1 T-wave magnitude has an inverted HR dependency, T-wave amplitude increases when HR decreases.

We believe that these differences between the two LQTS groups are linked to the abnormal kinetics of the delayed rectifier potassium currents of the myocardium cells. It is the efflux of potassium ions that produces the T-wave of the electrocardiogram. Agents that delay or prevent this movement of potassium will modify the appearance of the T-wave. More precisely, IKr is a current moving potassium ions out of the cardiac cells during the plateau phase of the action potential. One may expect to see changes on the surface ECG recordings in the late part of the T-wave.

Clinical Usefulness of Repolarization Morphology

Genotype identification by ECG is useful for stratifying molecular genetic studies. With 5 disease genes and 170 mutations already identified, it is very costly and time consuming to screen all known genes and mutational sites, limiting the application of genetic studies. With a typical ECG pattern, the suspected gene can be the initial target for testing, with a higher likelihood of rapid identification of the mutation. Such a strategy will significantly reduce time and costs, allowing more families to be genotyped and enhancing genotype-phenotype correlation studies. Furthermore, if therapeutic interventions based on specific genotype are shown to be effective, genotype identification by ECG could be helpful for therapeutic decision-making. These findings are applicable only to patients and families with an established clinical diagnosis of LQTS, from LQT1 and LQT2 mutations.

The multivariate analysis demonstrated that the use of very simple measurements such a the amplitude of the T-wave, the length of specific intervals such as TpTe provides excellent discrimination between LQT1 and LQT2 patients. Thus, the need for more sensitive quantifiers does not seem to bring a significant improvement (~+8% sensitivity). It is noteworthy that in case of smaller inhibition of IKr current such as in drug induced LQTS such parameters may become more useful.

We evidenced very different behavior of T-wave magnitude between the two types of mutation across heart rate. Such observation may be very interesting and should be investigated further. One may imagine designing a simple test in which the T-wave magnitude and RR relationship may be modeled in order to identify a loss of relationship, according to our observation in LQT2 patients such loss seems to characterize patients with IKr-inhibition. Such test may be applicable to the congenital and drug-induced LQTS.

Identifying IKr or IKs-related abnormalities of the surface ECGs may find broader application than discriminating the type of congenital LQTS, in a more general population estimating the propensity of an individual to the drug-induced LQTS is a relevant question. The drug-induced QT prolongation and the development of lethal arrhythmias of an individual due to a compound affecting the kinetics of the ion currents of the myocardial cells, depends on numerous factors including the individual genetic make-up. Thus, an individual predisposition to certain compound could be assessed based on ECG factors or the development of electrocardiographic signs for a predisposition to cardiac events on certain drug could be evaluated. Although this test was not able to screen normal people from those with mutations, it is possible that similar models may be developed to screen normal patients from those with LQT1 and LQT2 in addition to being able to differentiate between LQT1 carriers and LQT2 carriers.

We demonstrated that LQT1 and LQT2 patients have specific phenotypic expressions of their mutation on the surface ECG and these expressions can be quantified using simple parameters to discriminate these two types of mutations. We evidenced different behaviors of T-wave magnitude between mutations across heart rate. Finally, we developed a binary logistic model computing the probability of a LQTS patient to carry an HERG mutation based on simple ECG parameters.

Figure 9:
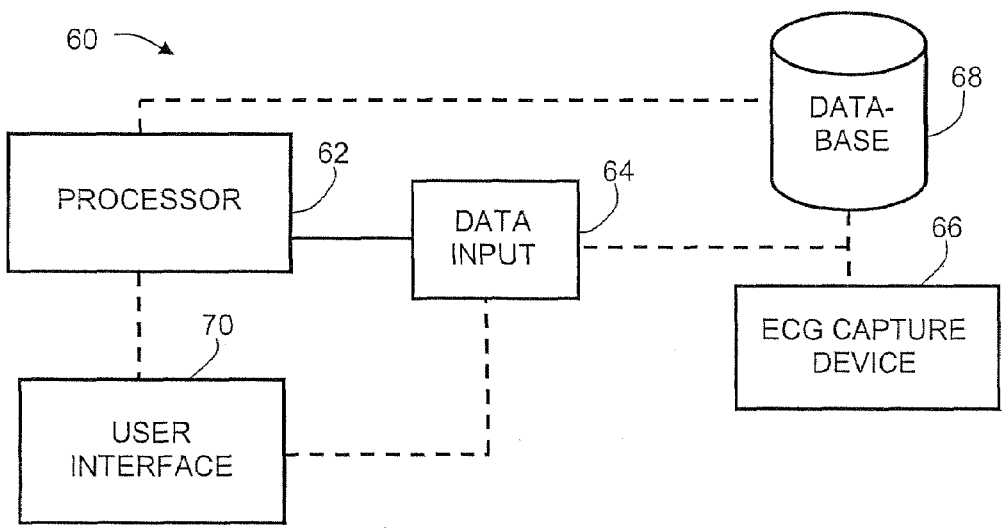
FIGS. 9-10 schematically illustrate embodiments of systems for differentiating between LQT1 and LQT2 mutation.

FIG. 9 schematically illustrates an embodiment of a system 60 for differentiating between LQT1 and LQT2 carriers in people with Long QT Syndrome. The system has a processor 62 which is configured to determine a scalar or a vector-based heart metric or parameter as discussed above. The processor 62 may be a computer executing machine readable instructions which are stored on a CD, a magnetic tape, an optical drive, a DVD, a hard drive, a flash drive, a memory card, a memory chip, or any other computer readable medium. The processor 62 may alternatively or additionally include a laptop, a microprocessor, an application specific integrated circuit (ASIC), digital components, electrical components, or any combination thereof. The processor 62 may be a stand-alone unit, or it may be a distributed set of devices.

A data input 64 is coupled to the processor 62 and configured to provide the processor with ECG data. An ECG capture device 66 may optionally be coupled to the data input 64 to enable the live capture of ECG data. Examples of ECG capture devices include, but are not limited to, a twelve-lead ECG device, an eight-lead ECG device, a two lead ECG device, a Holter device, a bipolar ECG device, and a uni-polar ECG device. Similarly, a database 68 may optionally be coupled to the data input 64 to provide previously captured ECG signal data to the processor. Database 68 can be as simple as a memory device holding raw data or formatted files, or database 68 can be a complex relational database. Depending on the embodiment, none, one, or multiple databases 68 and/or ECG capture devices 66 may be coupled to the data input 64. The ECG capture device 66 may be coupled to the data input 64 by a wired connection, an optical connection, or by a wireless connection. Suitable examples of wireless connections may include, but are not limited to, RF connections using an 802.11x protocol or the Bluetooth® protocol. The ECG capture device 66 may be configured to transmit data to the data input 64 only during times which do not interfere with data measurement times of the ECG capture device 66. If interference between wireless transmission and the measurements being taken is not an issue, then transmission can occur at any desired time. Furthermore, in embodiments having a database 68, the processor 62 may be coupled to the database 68 for storing results or accessing data by bypassing the data input 64.

The system 60 also has a user interface 70 which may be coupled to either the processor 62 and/or the data input 64. The user interface 70 can be configured to display the ECG signal data, a statistical plot of LQT1 vs LQT2 determination based on the ECG signal data, and/or an overall determination of LQT1 vs LQT2 status with or without confidence indicators. The user interface 70 may also be configured to allow a user to select ECG signals from a database 68 coupled to the data input 64, or to start and stop collecting data from an ECG capture device 66 which is coupled to the data input 64.

Figure 10:
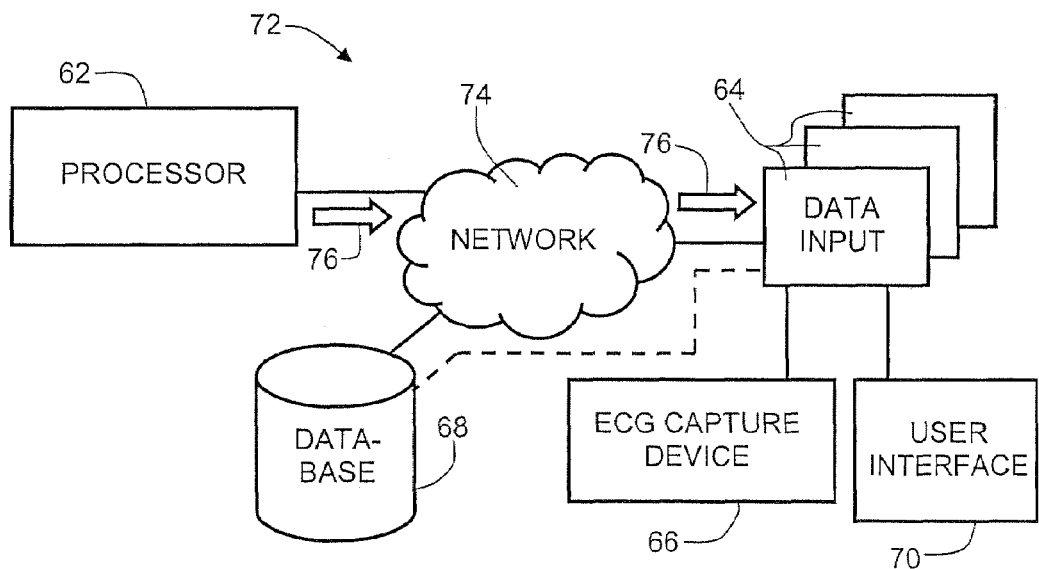

FIG. 10 schematically illustrates another embodiment of a system 72 for assessing repolarization abnormalities. In this embodiment, the processor 62 is set-up to be a remote processor which is coupled to the data input 64 over a network 74. The network 74 may be a wired or wireless local area network (LAN or WLAN) or the network 74 may be a wired or wireless wide area network (WAN, WWAN) using any number of communications protocols to pass data back and forth. Having a system 72 where the processor 62 is located remotely allows multiple client side data inputs 64 to share the resources of the processor 62. ECG signals may be obtained by the data input 64 from a database 68 and/or an ECG capture device 66 under the control of a user interface 70 coupled to the data input 64. The ECG signal data may then be transferred over the network 74 to the processor 62 which can then determine whether the subject of the ECG is an LQT1 or an LQT2 carrier and transmit data signals 76 having an indication of whether a patient is an LQT1 carrier or an LQT2 carrier to the client side. Such data transmissions may take place over a variety of transmission media, such as wired cable, optical cable, and air. In this embodiment, the remote processor 62 can be used to help keep the cost of the client-side hardware down, and can facilitate any upgrades to the processor or the instructions being carried out by the processor, since there is a central upgrade point.

Figure 8:
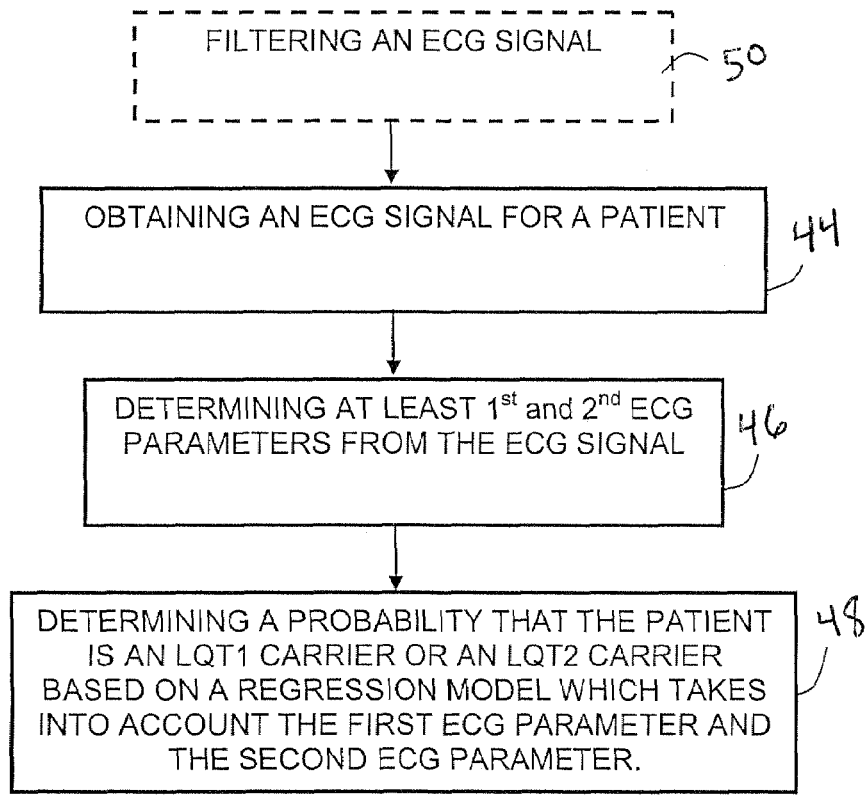
FIG. 8 illustrates one embodiment of a method for differentiating between LQT1 and LQT2 mutation.

FIG. 8 illustrates one embodiment of a method for differentiating between LQT1 and LQT2 carriers for those who have Long QT Syndrome. An ECG signal is obtained 44, either from an ECG capture device or from an ECG storage device. The ECG signals may be obtained in "real-time" from a subject, or the ECG signals may be obtained from a database (which should be understood to include memory devices) storing previously obtained ECG signals. At least first and second ECG parameters are determined 46 from the ECG signal. Example parameters have been discussed above, and may include, but are not limited to scalar parameters, such as Tmagnitude, TpTe, RR, QT, QTc, left slope of the T-wave, right slope of the T-wave, and QTpeak. Example parameters may also include, but are not limited to vector-based parameters, such as left slope of the ev1 T-wave, right slope of the ev1 T-wave, MV, and Loop QT offset. Finally, a probability is determined 48 on whether the patient is an LQT1 carrier or an LQT2 carrier based on a regression model which takes into account the first ECG parameter and the second ECG parameters. Non-limiting examples of models which may be used to see if someone is an LQT2 carrier are:

LQT2 prediction: $\log(\text{odds}) = \log(p2/(1/p2)) = -7.19 - 15.70(T\text{mag}) + 0.10(TpTe)$     (Example 1)

LQT2 prediction: $\log(\text{odds}) = \log(p2/(1-p2)) = 11.7 - 1.35(RS\ T) - 0.32 QTp + 0.25(T\text{-loop } QT)$     (Example 2)

LQT2 prediction: $\log(\text{odds}) = 11.73 - 1352(\alpha R \text{ on } ev1) + 0.2480(\text{Loop Offset } QT) - 0.3163(QT\text{peak from Lead II})$     (Example 3)

It should be understood that the LQT2 prediction examples above could be converted to LQT1 probabilities instead.

Other embodiments may include a filtering 50 step which may include statistical combinations of multiple beats from the ECG signals. As a non-limiting example, a median beat may be created from a number of consecutive beats from each lead. In some embodiments, one or more leading beats may be discarded. In other embodiments, one or more trailing beats may be discarded. In further embodiments, only beats with a stable heart rate may be taken into account. An example of a suitable definition of beats with a stable heart rate is when the heart rate for a given beat varies less than ten percent in beats of the previous two minutes. In other embodiments other percentages, time-frames, and definitions of a stable heart rate may be used without deviating from the scope of the claimed invention.

The advantages of a method and system to differentiate between LQT1 and LQT2 carriers have been discussed herein. Embodiments discussed have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A method differentiating LQT1 mutation from LQT2 mutation, comprising:
   obtaining an ECG signal for a patient;
   determining at least a first ECG parameter and a second ECG parameter from the ECG signal; and
   determining a probability that the patient is an LQT1 carrier or an LQT2 carrier based on a regression model which takes into account the first ECG parameter and the second ECG parameter.

2. The method of claim 1, wherein the ECG signal is obtained from a database.

3. The method of claim 1, wherein the ECG signal is obtained from an ECG capture device.

4. The method of claim 1, wherein the first and second ECG parameters are selected from the group consisting of QT-peak interval, and Tpeak-to-Tend interval.

5. The method of claim 1, wherein a probability that the patient is an LQT2 carrier is determined by the following formula:

$$\log(\text{odds}) = K + C1(P1) + C2(P2),$$

where K is a constant, C1 is a first coefficient, C2 is a second coefficient, P1 is the first ECG parameter, and P2 is the second ECG parameter.

6. The method of claim 5, wherein:
K equals approximately −7.19;
C1 equals approximately −15.70;
C2 equals approximately 0.10;
P1 is T-wave amplitude; and
P2 is TpTe.

7. The method of claim 1, further comprising determining a third ECG parameter, and wherein a probability that the patient is an LQT2 carrier is determined by the following formula:

$$\log(\text{odds}) = K + C1(P1) + C2(P2) + C3(P3),$$

where K is a constant, C1 is a first coefficient, C2 is a second coefficient, C3 is a third coefficient, P1 is the first ECG parameter, P2 is the second ECG parameter, and P3 is the third ECG parameter.

8. The method of claim 7, wherein:
K equals approximately 11.7;
C1 equals approximately −1.35;
P1 is RS T;
C2 equals approximately −0.32;
P2 is QTp;
C3 equals approximately 0.25; and
P3 is T-loop QT.

9. The method of claim 7, wherein:
K equals approximately 11.73;
C1 equals approximately −1352;
P1 is a right slope of a Twave from ev1;
C2 equals approximately 0.2480;
P2 is a QT loop offset;
C3 equals approximately −0.3163; and
P3 is a peak of a QT interval.

10. The method of claim 9, wherein the peak of the QT interval is taken from Lead II on an ECG capture device.

11. The method of claim 1, wherein obtaining the ECG signal comprises filtering the ECG signal.

12. The method of claim 11, wherein filtering the ECG signal comprises low-pass FIR filtering the ECG signal.

13. The method of claim 11, wherein filtering the ECG signal comprises removing a wandering baseline.

14. The method of claim 11, wherein filtering the ECG signal comprises statistically combining multiple beats from the ECG signal.

15. The method of claim 14, wherein statistically combining multiple beats from the ECG signal comprises creating a median beat.

16. The method of claim 11, wherein filtering the ECG signal comprises discarding one or more leading beats from the ECG signal.

17. The method of claim 11, wherein filtering the ECG signals comprises discarding one or more trailing beats from the ECG signal.

18. The method of claim 11, wherein filtering the ECG signals comprises discarding beats which do not have a corresponding stable heart rate.

19. The method of claim 18, wherein discarding beats which do not have a corresponding stable heart rate comprises discarding beats which have a heart rate that varies by more than a certain percentage in a previous arbitrary time frame.

20. The method of claim 19, wherein the certain percentage is ten percent and the arbitrary time frame is two minutes.

21. The method of claim 11, wherein filtering the ECO signal comprises sorting beats in the ECG signal into heart rate bins.

22. The method of claim 21, wherein the first and second parameters are calculated only for a specific heart rate bin.

23. The method of claim 22, wherein the specific heart rate bin comprises heart beats having a duration of approximately 775-800 milliseconds.

24. A computer readable medium having stored thereon instructions for differentiating between LQT1 and LQT2 mutations, which, when executed by a processor, causes the processor to perform the steps according to claim 1.

25. A method of therapeutic decision making, comprising:
obtaining an ECG signal for a patient;
determining at least a first ECG parameter and a second ECG parameter from the ECG signal;
determining a probability that the patient is an LQT1 carrier or an LQT2 carrier based on a regression model which takes into account the first ECG parameter and the second ECG parameter; and
taking a therapeutic action based on the probability that the patient is an LQT1 carrier or an LQT2 carrier.

26. The method of claim 25, wherein taking a therapeutic action based on the probability that the patient is an LQT1 carrier or an LQT2 carrier comprises:
prescribing a medication which has reduced or no interaction with an LQT1 condition if the patient has a probability of being an LQT1 carrier; or
prescribing a medication which has reduced or no interaction with an LQT2 condition if the patient has a probability of being an LQT2 carrier.

27. The method of claim 25, wherein taking a therapeutic action based on the probability that the patient is an LQT1 carrier or an LQT2 carrier comprises prescribing genetic screening to confirm a genetic mutation.

28. The method of claim 25, wherein taking a therapeutic action based on the probability that the patient is an LQT1 carrier or an LQT2 carrier comprises instructing the patient to stop taking a medication.

* * * * *

UNITED STATES PATENT AND TRADEMARK OFFICE
CERTIFICATE OF CORRECTION

PATENT NO. : 7,623,910 B2 Page 1 of 1
APPLICATION NO. : 11/685016
DATED : November 24, 2009
INVENTOR(S) : Couderc et al.

It is certified that error appears in the above-identified patent and that said Letters Patent is hereby corrected as shown below:

Claim 21, at Column 12, Line 56: Delete "ECO" and insert --EC$\underline{G}$--

Signed and Sealed this

Second Day of February, 2010

David J. Kappos
*Director of the United States Patent and Trademark Office*